United States Patent [19]

Ichikawa et al.

[11] 3,963,787

[45] June 15, 1976

[54] PROCESS FOR PRODUCING DIPHENYLS

[75] Inventors: Yataro Ichikawa; Teizo Yamaji, both of Iwakuni, Japan

[73] Assignee: Teijin Limited, Osaka, Japan

[22] Filed: Jan. 24, 1973

[21] Appl. No.: 326,523

Related U.S. Application Data

[63] Continuation-in-part of Ser. No. 60,945, Aug. 4, 1970, abandoned.

[52] U.S. Cl. .................. 260/613 R; 260/649 DP; 260/670
[51] Int. Cl.² ................. C07C 43/20; C07C 25/00; C07C 15/14
[58] Field of Search .................. 260/670, 613 R

[56] References Cited
UNITED STATES PATENTS

| | | | |
|---|---|---|---|
| 3,145,237 | 8/1964 | Helden et al. | 260/670 |
| 3,401,207 | 9/1968 | Selwitz | 260/670 |
| 3,547,982 | 12/1970 | McKeon et al. | 260/488 CD |

OTHER PUBLICATIONS

Davidson et al., Chem. and Ind., p. 457, (1966), p. 1361, (1967).

Blumenthal, "The Chemical Behavior of Zirconium", pp. 119–123, 135–144 and 311–338, (1958).

*Primary Examiner*—Bernard Helfin
*Assistant Examiner*—Nicky Chan
*Attorney, Agent, or Firm*—Sherman & Shalloway

[57] ABSTRACT

The oxidative coupling of benzene or benzene derivatives to form the corresponding diphenyls, comprising contacting benzene or a benzene derivative, such as toluene, with molecular oxygen using as a catalyst organic carboxylates of palladium such as palladium acetate. Use of at least one zirconium compound such as zirconium oxystearate in conjunction with the catalyst gives rise to an increased catalytic activity. The diphenyls are intermediates for production of dyestuffs, pharmaceuticals and other chemicals, and also find application in the preparation of high-molecular-weight polyesters and polyamides.

4 Claims, No Drawings

PROCESS FOR PRODUCING DIPHENYLS

This application is a continuation-in-part application of application Ser. No. 60,945 filed Aug. 4, 1970, now abandoned.

This invention relates to a process for producing diphenyls by contacting benzene or benzene derivatives with molecular oxygen in a liquid phase thereby to dimerize them oxidatively. More specifically, the invention relates to a process for producing diphenyls wherein the oxidative coupling of benzene or benzene derivatives is carried out in the presence of an organic carboxylate of palladium as a catalyst.

The method of producing diphenyl compounds by dimerization of benzene or alkylbenzenes is interesting both scientifically and technologically.

The methods heretofore known include one wherein palladium chloride is reacted with an aromatic compound in the presence of an acid binder such as sodium acetate, or one wherein benzene or toluene is reacted with palladium acetate in acetic acid in the presence of an acid such as perchloric acid or sulfuric acid or an alkali salt such as sodium acetate or an alkaline earth metal.

In the method involving the use of palladium chloride and an acid binder, there are problems such as the corrosion of equipment by palladium chloride, and the production of acetate as by-product by the addition of an alkali salt such as sodium acetate as the acid binder. Especially with alkylbenzenes, increased amounts of by-products such as benzyl acetate pose a problem. Furthermore, the method involving the addition of perchloric acid or sulfuric acid also has the defect of corrosion of the eqiupment.

In the prior art processes described above, the palladium compound mainly acts as a reactant of stoichiometrical amount, and the palladium compound which has participated in the dimerization reaction is reduced to a low valency state. Thus, it does not have a high valency effective for the dimerization in the reaction system, and cannot act catalytically. In view of the fact that palladium is a very valuable metal, the prior art processes are not advantageous for the commercial production of diphenyl compounds from aromatic compounds, especially alkyl benzenes.

Accordingly, a primary object of the invention is to provide a process for producing diphenyls by the oxidative coupling of benzene or benzene derivatives using a palladium compound catalytically. The other objects and advantages of the invention will become apparent from the following description.

According to the present invention, benzene or benzene derivatives expressed by the following formula

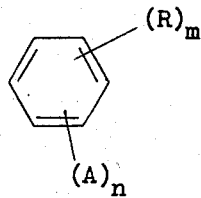

(1)

wherein R's may be the same or different and represent an alkyl group having 1–4 carbon atoms;
$m$ is a positive integer of 0 to 4;
A's may be the same or different and represent an alkoxy group having 1–4 carbon atoms or a halogen atom;
$n$ is a positive integer of 0–2; and the sum of $m$ and $n$ does not exceed 4, and when $m$ is 0 or $n$ is 0, $0(R)_m$ or $-(A)_n$ respectively represents a hydrogen atom, are contacted with molecular oxygen, at a pressure of at least 2 atmosphere calculated as the partial pressure of oxygen and at a temperature in the range of 100° to 300°C, in the presence of at least one organic carboxylate of palladium as a catalyst, the amount of said catalyst being at least $1 \times 10^{-5}$ gram-atom calculated as metallic palladium, for each gram molecule of benzene or its derivatives, thereby to produce the corresponding diphenyls catalytically.

The compounds used as the starting material in the present invention may be any compounds that come within the formula (1) given above, and the specific examples are:

A. benzene;
B. monoalkyl benzenes such as toluene, ethylbenzene and isopropylbenzene;
C. dialkyl benzenes, for instance, xylenes such as o-xylene and m-xylene, diethylbenzenes such as m-diethylbenzene or o-diethylbenzene, diisopropyl benzenes such as o-diisopropyl benzene and m-diisopropyl benzene, o-, m-, or p-ethyltoluene, o-, m-, or p-isopropyltoluene;
D. trialkyl benzenes such as 1,2,3-trimethylbenzene, 1,2,4-trimethylbenzene, 1,3,5-trimethylbenzene, 1,2,4-triethylbenzene, 1,2-dimethyl-4-ethylbenzene, and 1,3-dimethyl-4-ethylbenzene;
E. monoalkoxybenzenes such as methoxybenzene (anisole), ethoxybenzene, n- or i-propoxybenzene, n- or i-butoxy benzene, and dialkoxybenzenes such as o-, m-, or p-dimethoxybenzene, and o-, m-, or p-diethylbenzene;
F. alkoxyalkyl benzenes such as o-, m-, or p-methoxy toluene, o-, m- or p-methoxy ethylbenzene, and o-, m- or p-ethoxytoluene;
G. halogenated benzenes such as monochlorobenzene, o-, m- or p-dichlorobenzene, monobromobenzene, o- or m-dibromobenzene, and o-, m- or p-monochloromonobromobenzene; and,
H. o-, m- or p-monochlorotoluene, o-, m- or p-monobromotoluene, monochloroxylene, monobromo xylene, and o-, m- or p-methoxychlorobenzene.

As the starting materials of the present invention, those of the formula (1) wherein R is a lower alkyl group having 1 to 3 carbon atoms, $m$ is 1, 2, or 3 and $n$ is 0, or alkylbenzenes wherein $m$ is 1 or 2 and which have one or two halogen atoms, especially chlorine atoms, as the $-(A)_n$ are preferred. Especially preferred starting materials are benzene, toluene, ortho- and/or meta-xylene.

The reaction by the process of the invention of oxidatively coupling the aforementioned starting materials is performed in a liquid phase either in the presence or absence of solvent using the palladium catalyst described below. When the reaction is carried out in the absence of a solvent, the reaction system is maintained liquid by the starting materials, and when it is carried out using a solvent, an organic liquid medium which is stable under the reaction conditions and inert to the reaction of the present invention is employed.

In the present invention, the oxidative coupling of the starting materials described above is carried out in the presence of a catalyst comprising at least one organic carboxylate of palladium. The organic carboxylates of palladium may be any of those which are at least partially soluble in the reaction system of the invention. Organic carboxylic acids which provide acid residues of such organic carboxylates may include any of aliphatic carboxylic acids, alicyclic carboxylic acids and aromatic carboxylic acids; they may not only be monocarboxylic acids, but also dibasic or polybasic carboxylic acids. Examples of the organic carboxylates of palladium which are conveniently used in the process of the invention are:

i. aliphatic monocarboxylates having 1–20 carbon atoms such as formate, acetate, trifluoroacetate, monochloroacetate, propionate, n- or iso-butyrate, laurate, palmitate, and stearate;

ii. aliphatic carboxylates such as naphthenate, cyclohexanemonocarboxylate, and methyl cyclohexanemonocarboxylate; and iii. benzenecarboxylates or naphthalenecarboxylates such as benzoate, o-, m-, or p-toluylate, phthalate, p-tertiary butylbenzoate, o-, m-, p-methoxybenzoate, chlorobenzoate and naphthate.

When the reaction of the invention is carried out in the presence of an organic carboxylic acid to be described hereinbelow or its aqueous solution as the organic liquid medium the aforementioned organic carboxylates of palladium can be formed in the reaction system of the present invention. Such organic carboxylates are utilized similarly as the catalyst for the reaction of the invention. The compounds which can form organic carboxylates of palladium in the reaction system of the invention may be any of those which can form salts by reaction with the aforementioned organic carboxylic acids. The preferred examples are inorganic compounds of palladium such as palladium oxides, hydroxides, nitrates or perchlorates, and suitable organic compounds of palladium.

The aforementioned organic carboxylates of palladium may be used singly or in combination of two or more as the catalyst for the reaction of the invention. In the process of the present invention, the palladium catalyst having a high valency effective for the reaction is reduced by the oxidative dimerization of the benzene, or its derivatives to a lower valency state, but is immediately oxidized and regenerated by the molecular oxygen present in the reaction system, thus maintaining a catalytic activity. Therefore, the palladium catalyst of the invention can be used even in very small amounts, and the amount of the catalyst used in the invention is not particularly restricted. In general, the amount of the catalyst is at least $1 \times 10^{-5}$ gram-atom, calculated as metallic palladium, for each gram-mol of the benzene or its derivatives used on the starting material, particularly preferred being 0.01 – 0.1 gram-atom. The upper limit of the amount of the palladium catalyst used in the invention is determined by economic and other factors, and not critical by itself.

The aforementioned organic carboxylates of palladium when used conjointly with a zirconium compound, can give the intended diphenyls in high yields with an increased catalytic activity. An especially outstanding rise in catalytic activity is observed when the zirconium compound is added to the organic carboxylate of palladium.

Such zirconium compound may be any of those which are partially soluble in the reaction system of the present invention, and suitable examples include, for instance, (a) organic carboxylates of zirconium, (b) oxycarboxylates of zirconium, (c) halogen compounds of zirconium, and (d) oxyhalogen compounds of zirconium. As the organic carboxylic acids which can provide carboxylic acid residues of the organic carboxylates of zirconium mentioned in (a) above, the same organic carboxylates as listed under paragraphs (i), (ii) and (iii) can be used. These organic carboxylates of zirconium are prepared by using the organic carboxylic acids and inorganic compounds capable of forming the salts of zirconium, such as the hydroxide, nitrate, perchlorate, and oxide of zirconium, and other suitable organic compounds of zirconium. Examples of the preferred organic carboxylates of zirconium include formate, acetate, propionate, n- or iso-butyrate, benzoate, and naphthenate.

The acids capable of providing the oxycarboxylic acid residues of the oxycarboxylates of zirconium may be any of the aforementioned organic carboxylic acids having an oxy group. Suitable examples of the oxycarboxylic acids include oxyformic acid, oxyacetic acid, oxypropionic acid, oxy n- or oxy iso-butyric acid. These oxycarboxylates of zirconium can be prepared by the same salt-forming reaction as used in the preparation of the organic carboxylates mentioned above.

As the halogen compounds of zirconium under (c) above, any of the halides such as chloride, bromide, iodide, and fluoride of zirconium can be used, the chloride and bromide being preferred.

Examples of the oxyhalogen compounds of zirconium mentioned under (d) above include, for instance, oxychloride, oxybromide or oxyiodide or zirconium, and the oxychloride is preferred.

These zirconium compounds (a), (b), (c) and (d) may be formed in the reaction system of the present invention in the same way as in the case of the organic carboxylates described above. These zirconium compounds can be present in the reaction system of the present invention either alone or in admixtures of two or more.

The amount of the zirconium compound used in the process of the present invention is not particularly restricted. But in general, it is 0.01 – 100 gram-atoms, preferably 0.1 – 50 gram-atoms, calculated as zirconium metal, per gram-atom of palladium of the palladium catalyst.

The catalyst comprising said palladium and zirconium may further contain compounds of Pt, Rh, Ir, Au, or Ag, which are partially soluble in the reaction system of the present invention, especially organic acid salts of these compounds or the oxides or hydroxides of these compounds which can form organic acid salts in an organic carboxylic acid solvent.

According to the process of the invention, the conjoint use of the zirconium compound makes it possible to cause palladium to act catalytically, and to obtain diphenyls in high yields.

Furthermore, in the present invention, an organic acid salt, carbonate, bicarbonate, or oxide, etc. of an alkali metal may be used as a catalyst conjointly with the organic carboxylate of palladium. This conjoint use can result in the preparation of diphenyls with high catalyst activity. The alkali metal compound used for this purpose is preferably a monocarboxylic acid salt such as acetic, propionic or butyric acid salt, carbonate, bicarbonate or oxide of potassium or sodium.

As previously stated, an inert organic liquid medium may be present in the reaction system of the present invention. The amount of such medium is usually not more than 100 times the weight of the benzene or benzene derivatives used as the starting material. The typical example of such inert organic liquid medium is an organic carboxylic acid. Examples of the preferred organic carboxylic acid are those which are liquid under the reaction conditions, preferably those which are liquid at room temperature, such as acetic acid, propionic acid, n- or iso-butyric acid. Aromatic or alicyclic carboxylic acids such as benzoic acid or naphthenic acid may also be used. Aqueous solutions of these carboxylic acids containing not more than 15 % by weight of water can also be used as the reaction medium.

Also an inert liquid compound, preferably liquid which is liquid under the reaction condition of the invention, such as aliphatic hydrocarbons, halogenated hydrocarbons, esters, ketones and ethers, can also be used as the reaction medium. Specific examples of such inert liquid compound are:

A. aliphatic hydrocarbons such as hexane, heptane and octane;
B. alicyclic hydrocarbons such as cyclopentane and cyclohexane;
C. chlorides and bromides of (A) or (B);
D. aliphatic ethers or alicyclic ethers such as methyl ether, ethyl ether, propyl ether, cyclopentyl ether, and cyclohexyl ether;
E. esters of aliphatic carboxylic acids such as methyl acetate, ethyl propionate and cyclohexyl acetate; and
F. aliphatic ketones or alicyclic ketones such as acetone, di-t-butyl ketone and dicyclohexyl ketone.

In the present invention, the oxidative coupling of the benzene or benzene derivative can be carried out catalytically by contacting the benzene or benzene derivatives with molecular oxygen in a liquid phase in the presence of the aforementioned palladium catalyst or in the presence of said palladium catalyst and the aforesaid zirconium compound, thereby to obtain diphenyls corresponding to the starting materials. For ensuring a smooth proceeding of the oxidative coupling reaction of the present invention, the reaction system is heated at a temperature in the range of 100° to 300°C., especially 110° to 250°C. The reaction is carried out advisably at a temperature in the range of 110° to 250°C., especially 120° to 250°C.

The molecular oxygen used in the practice of the present invention may be pure oxygen or a gas-containing molecular oxygen which is diluted with an inert gas such as nitrogen, argon, helium or carbon dioxide, an example being air. It is quite important that such molecular oxygen or molecular oxygen-containing gas be contacted with the benzene or benzene derivatives at a pressure of at least 2, preferably at least 3 atmosphere calculated as the partial pressure of oxygen in order to perform the dimerization reaction catalytically and to obtain the diphenyls in high yield. No specific upper limit is set on the partial pressure of oxygen in the molecular oxygen or molecular oxygen-containing gas. Too high a partial oxygen pressure, however, is commercially undesirable, and suitable pressures are generally below 300 atmospheres.

The process of the invention can be practised either by the batchwise, intermittent, continuous or circulating method. The wall of a reactor used in the invention may be of any materials which exhibit resistance to corrosion. If no solvent is used, the materials may be iron. Generally, however, stainless steel is suitable, and examples of other materials, that can be used include Hastelloy B, Hastelloy C, silver, nickel, titanium, titanium alloy, tantalum, glass lining and fluorine resin lining.

The diphenyls obtained by the process of the invention are separated from the reaction mixture by such procedures as evaporation, distillation, filtration or centrifugation according to their physical characteristics, and can be purified by any means usually employed in the art.

According to the process of the invention, it is advantageous to separate the diphenyls from the reaction mixture at a temperature below 350°C., preferably below 300°C. By separating the diphenyls from the reaction mixture at these temperatures, the catalysts can still remain highly active in the residual reaction mixture. Hence, it is possible to use the catalysts in an active state contained in the residual reaction mixture with or without separation therefrom, and recycle them for further use. The separation of the active catalysts from the residual solvent can be effected by any known means such as extraction and recrystallization.

As previously stated, benzene or benzene derivatives can be converted to the corresponding diphenyls by a one-step catalytic reaction in accordance with the present invention, and a very small amount of the above-described palladium catalyst or the palladium-zirconium catalyst exhibits an effective catalytic activity in the reaction, giving the diphenyls in high yields and with high selectivities. The palladium or palladium-zirconium catalyst can be recovered, and recycled for further use.

The diphenyls obtained by the process of the invention can be used as intermediates for production of dyestuffs, pharmaceuticals and various other chemicals. Or after being converted to carboxylic acids or their esters, these diphenyls are used as the polybasic acid components in the synthesis of high molecular weight polyamides or unsaturated polyesters.

The invention will further be described by the following Examples, which are intended to be illustrative rather than limitative. Unless otherwise specified, all parts in the Examples are parts by weight.

EXAMPLE 1

A stainless steel autoclave equipped with a stirrer was charged with 15 parts of toluene, 32 parts of glacial acetic acid and 0.42 part of palladium acetate [Pd(OAc)$_2$], and the toluene was reacted for 4 hours at 130°C. with the introduction of oxygen at a partial pressure of 100 kg/cm$^2$G. Gas-chromatographic analysis of the product indicated the formation of 0.744 part of dimethyl diphenyl, which corresponded to 219 mol % of the palladium acetate fed. This shows that the palladium salt acted catalytically.

EXAMPLE 2

The procedure of Example 1 was repeated except that the reaction temperature was maintained at 150°C. There was obtained 0.628 part of dimethyl diphenyl, which corresponded to 185 mol % based on the palladium salt fed.

COMPARATIVE EXAMPLE 1

A stainless steel autoclave equipped with a stirrer was charged with 3 parts of toluene, 15 parts of glacial acetic acid, and 0.42 part of palladium acetate [Pd(OAc)$_2$], and the toluene was reacted for 4 hours at 90°C. with the introduction of oxygen at a partial pressure of 60 kg/cm$^2$G. A small amount of benzyl acetate and 0.0687 part of dimethyl diphenyl were obtained, and the precipitation of palladium metal was observed. The dimethyl diphenyl so obtained was in an amount of only 20.2 mol % based on the palladium salt fed. The rate of dimerization was slow, and the palladium salt was precipitated as metal. This shows that the palladium catalyst was not regenerated by oxidation, and did not act catalytically.

COMPARATIVE EXAMPLE 2

A glass reactor was charged with 15 parts of toluene, 32 parts of acetic acid, and 0.42 part of palladium acetate, which were refluxed under stirring for 4 hours in an atmosphere of oxygen at a temperature of 110°C. There was obtained 0.238 part of dimethyl diphenyl, and metal palladium was precipitated. The dimethyl diphenyl so produced was in an amount of 70 mol % based on the palladium salt fed. The metal palladium was not regenerated by oxidation, and did not act catalytically.

EXAMPLE 3

A stainless autoclave equipped with a stirrer was charged with 10 parts of toluene, 32 parts of acetic acid and 0.42 part of palladium acetate, and the toluene was reacted for 10 hours at 110°C. with the introduction of oxygen at a partial pressure of 2 kg/cm$^2$G. There was obtained dimethyl diphenyl in an amount of 181 mol % based on the palladium salt fed.

EXAMPLE 4

A stainless steel autoclave equipped with a stirrer was charged with 10 parts of benzene, 32 parts of glacial acetic acid, and 0.42 part of palladium acetate [Pd(OAc)$_2$], and the benzene was reacted for 5 hours at 135°C. with the introduction of oxygen at a partial pressure of 60 kg/cm$^2$G. There was obtained 0.756 part of diphenyl, which corresponded to 263 mol % of the palladium acetate fed.

EXAMPLE 5

A stainless steel autoclave equipped with a stirrer was charged with 8 parts of o-xylene, 32 parts of glacial acetic acid, and 0.42 part of palladium acetate [Pd(OAc)$_2$], and the o-xylene was reacted for 10 hours at 115°C. with the introduction of oxygen at a partial pressure of 20 kg/cm$^2$G. There was obtained tetramethyl diphenyl in a yield of 153 mol % based on the palladium salt fed.

EXAMPLE 6

An autoclave equipped with a stirrer was charged with 15 parts of toluene, 32 parts of glacial acetic acid and 0.42 part of palladium acetate, and the toluene was reacted for 7 hours at 95°C. with the introduction of oxygen at a partial pressure of 100 kg/cm$^2$G. There was obtained 0.372 part of dimethyl diphenyl, which corresponded to 109 mol % of the palladium salt fed.

EXAMPLE 7

An autoclave equipped with a stirrer was charged with 15 parts of toluene, 32 parts of glacial acetic acid and 0.42 part of palladium acetate, and the toluene was reacted for 30 minutes at 240°C. with the introduction of oxygen at a partial pressure of 100 kg/cm$^2$G. There was obtained 0.802 part of dimethyl diphenyl, which corresponded to 235 mol % of the palladium salt fed.

EXAMPLE 8

A stainless steel autoclave equipped with a stirrer was charged with 15 parts of toluene, 32 parts of glacial acetic acid and 0.42 part of palladium stearate, and the toluene was reacted for 4 hours at 130°C. with the introduction of oxygen at a partial pressure of 100 kg/cm$^2$G. Analysis of the product by gas chromatography indicated the formation of 0.452 part of dimethyl diphenyl. The amount corresponded to a yield of 133 mol % based on the palladium stearate fed. This shows that the palladium salt acted catalytically under these conditions.

EXAMPLE 9

The procedure of Example 3 was repeated except that 0.42 part of palladium naphthenate was used as the catalyst. There was obtained 0.395 part of dimethyl diphenyl, which corresponded to 116 mol % yield based on the palladium naphthenate fed. This shows that the palladium salt acted catalytically under these conditions.

EXAMPLE 10

A stainless steel autoclave equipped with a stirrer was charged with 15 parts of toluene, 32 parts of glacial acetic acid, 0.21 part of palladium acetate [Pd(OAc)$_2$], and 1.052 parts of zirconyl acetate [ZrO(OAc)$_2$], and the toluene was reacted for 4 hours at a temperature of 150°C. with the introduction of oxygen at a partial pressure of 100 kg/cm$^2$G. 3.2 Parts of toluene was reacted, and dimethyl diphenyl was obtained at a selectivity of 87 mol % based on the reacted toluene.

The amount of dimethyl diphenyl produced corresponded to 1619 mol % based on the palladium acetate fed. This shows that the palladium salt acted catalytically.

EXAMPLE 11

A stainless steel autoclave equipped with a stirrer was charged with 15 parts of toluene, 32 parts of glacial acetic acid, 0.42 part of palladium acetate [Pd(OAc)$_2$] and 2.105 parts of zirconyl acetate [ZrO(OAc)$_2$], and the toluene was reacted for 4 hours at 130°C. with the introduction of oxygen at a partial pressure of 60 kg/cm$^2$G. 14.7 Mol percent of the toluene was converted and dimethyl diphenyl was obtained in a yield of 79.1 mol % based on the converted toluene. The amount of the dimethyl diphenyl corresponded to 626.5 mol % of the palladium acetate fed. This shows that the palladium salt acted catalytically.

EXAMPLE 12

The procedure of Example 10 was repeated except that benzene was used instead of toluene. 2.5 grams of benzene was converted, and diphenyl was obtained in a yield of 82 mol % based on the benzene converted.

EXAMPLE 13

The procedure of Example 10 was repeated except that 20 parts of o-xylene was used instead of toluene. There was obtained 1.78 parts of tetramethyl diphenyl, which corresponded to 906.6 mol % based on the palladium acetate fed.

EXAMPLE 14

A stainless steel autoclave was charged with 30 parts of toluene, 16 parts of glacial acetic acid, 0.42 part of palladium acetate and 0.42 part of zirconyl acetate, and the toluene was reacted for 6 hours at 95°C. with the introduction of oxygen at a partial pressure of 60 kg/cm²G. There was obtained 0.384 part of dimethyl, diphenyl, which corresponded to 112.9 mol % based on the palladium acetate fed.

EXAMPLE 15

A stainless steel autoclave equipped with a stirrer was charged with 3 parts of toluene, 16 parts of glacial acetic acid, 0.42 part of palladium acetate and 0.42 part of zirconyl acetate, and the toluene was reacted for 8 hours at 130°C. with the introduction of oxygen at a partial pressure of 2 kg/cm²G. There was obtained 0.418 part of dimethyl diphenyl, which corresponded to 123 mol % based on the palladium acetate fed.

EXAMPLE 16

A stainless steel autoclave equipped with a stirrer was charged with 15 parts of toluene, 32 parts of glacial acetic acid, 0.21 part of palladium acetate, and 1.052 parts of zirconium oxystearate, and the toluene was reacted for 4 hours at 150°C. with the introduction of oxygen at a partial pressure of 100 kg/cm²G. Gas-chromatographic analysis of the reaction product indicated the formation of dimethyl diphenyl in an amount corresponding to 620 mol % based on the palladium acetate fed. This shows that the palladium salt acted catalytically.

EXAMPLE 17

The procedure of Example 16 was repeated except that 1.052 parts of zirconium oxybenzoate was used instead of the zirconium oxystearate. There was obtained dimethyl diphenyl of an amount corresponding to 540 mol % of the palladium acetate fed. This shows that the palladium salt acted catalytically under these conditions.

EXAMPLE 18

The procedure of Example 16 was repeated except that 1.052 parts of zirconium oxynaphthenate as used instead of the zirconium oxystearate. There was obtained dimethyl diphenyl of an amount corresponding to 730 mol % of the palladium acetate fed. This shows that the palladium salt acted catalytically under these conditions.

EXAMPLE 19

An autoclave equipped with a stirrer was charged with 15 parts of toluene, 32 parts of glacial acetic acid, 0.21 part of palladium acetate and 1.052 parts of zirconium oxychloride, and the toluene was reacted for 4 hours at 130°C. with the introduction of oxygen at a partial pressure of 60 kg/cm²G. There was obtained dimethyl diphenyl in an amount corresponding to 600 mol % based on the palladium salt fed. This shows that the palladium salt acted catalytically under these conditions.

EXAMPLES 20 to 24

An autoclave equipped with a stirrer was charged with 15 parts of toluene, 32 parts of glacial acetic acid, 0.42 part of palladium acetate and the metal acetylacetonate of the amount indicated in Table 1 below, and the toluene was reacted for 4 hours at 130°C. with the introduction of oxygen at a partial pressure of 60 kg/cm²G. The results obtained are shown in the following table. It is seen from these results that the palladium salt acted catalytically in all runs.

| Ex. No. | Acetyl- acetonate | Amount (parts) | Amount of di- methyl diphenyl produced (parts) | Yield based on the pal- ladium salt (mol %) |
|---|---|---|---|---|
| 20 | MoO$_2$(AA)$_2$ | 0.614 | 1.91 | 562 |
| 21 | TiO(AA)$_2$ | 0.494 | 0.81 | 238 |
| 22 | Cu(AA)$_2$ | 0.247 | 1.10 | 324 |
| 23 | K(AA) | 0.130 | 0.84 | 247 |
| 24 | — | — | 0.63 | 185 |

Note: In the table, AA shows an acetylacetone ligand.

EXAMPLE 25

An autoclave equipped with a stirrer was charged with 15 parts of methyl anisole, 32 parts of glacial acetic acid, 0.21 part of palladium acetate and 1.052 part of zirconium oxyacetate, and the reaction of the methyl anisole was performed for 4 hours at 150°C. with the introduction of oxygen at a partial pressure of 100 kg/cm²G. There was obtained dimethyldimethoxy diphenyl in an amount corresponding to 2053 mol % based on the palladium salt fed. This shows that the palladium salt acted catalytically.

EXAMPLE 26

The procedure of Example 25 was repeated except that 15 parts of chlorobenzene was used instead of the methyl anisole. There was obtained dichloro diphenyl in an amount corresponding to 934 mol % based on the palladium salt fed. This shows that the palladium salt acted catalytically.

EXAMPLE 27

The procedure of Example 25 was repeated except that 15 parts of o-chlorotoluene was used instead of the methyl anisole. There was obtained dichlorodimethyl diphenyl in an amount corresponding to 1114 mol % based on the palladium salt fed. This shows that the palladium salt acted catalytically.

EXAMPLE 28

A stainless steel autoclave equipped with a stirrer was charged with 15 parts of toluene, 32 parts of glacial acetic acid and 0.42 part of palladium acetate [Pd(OAc)$_2$], and the toluene was reacted for 4 hours at 130°C. with the introduction of oxygen at a partial pressure of 100 kg/cm²G. The reaction product was transferred to a distillation apparatus. Unreacted toluene and glacial acetic acid were removed by distillation at 130°C. Thereafter, the bath temperature was raised to 160°C. and the system was maintained at a pressure of 2 mmHg. Dimethyl diphenyl formed was distilled, and 0.901 part of dimethyl diphenyl was obtained. The resulting residue contained hardly any dimethyl diphenyl. Using it as a catalyst, the above mentioned procedure was repeated, and there was obtained 0.824 part of dimethyl diphenyl, which corresponded to 242 mol % based on the palladium fed. This shows that the palladium salt acted catalytically and the dimerization proceeded effectively.

EXAMPLE 29

A stainless steel autoclave equipped with a stirrer was charged with 15 parts of toluene, 32 parts of glacial acetic acid, 0.21 part of palladium acetate [Pd(OAc)$_2$] and 1.052 parts of zirconyl acetate [ZrO(OAc)$_2$], and the toluene was reacted for 4 hours at 150°C. with the introduction of oxygen at a partial pressure of 100 kg/cm$^2$G. The reaction product was transferred to a distillation apparatus, and unreacted toluene and acetic acid were removed by distillation at 130°C. at normal atmospheric pressure. Thereafter, the temperature of the bath was raised to 170°C. and the system was maintained at a pressure of 2 mmHg, thereby to remove dimethyl diphenyl by distillation. There was obtained 3.16 parts of dimethyl diphenyl. There was hardly any dimethyl diphenyl in the catalyst residue. Except using the recovered catalyst, the reaction was performed in the same manner as mentioned above to form 2.69 parts of dimethyl diphenyl, which corresponded to 87 mol % of the reacted toluene.

EXAMPLE 30

The procedure of Example 29 was repeated except that the removal of dimethyl diphenyl at the time of recovering the catalyst was effected with an aspirator at a bath temperature of 350°C. at reduced pressure. Dimethyl diphenyl was obtained in a yield of 105 mol % based on the palladium acetate fed.

COMPARATIVE EXAMPLE 3

The procedure of Example 29 was repeated except that dimethyl diphenyl was removed at the time of recovering the catalyst at a bath temperature of 380°C. and at normal atmospheric pressure. Dimethyl diphenyl was hardly produced.

EXAMPLE 31

A stainless steel autoclave equipped with a stirrer was charged with 20 parts of o-xylene, 32 parts of glacial acetic acid, 0.21 part of palladium acetate [Pd(AcO)$_2$] and 1.052 parts of zirconyl acetate [ZrO(AcO)$_2$], and the o-xylene was reacted for 4 hours at 150°C. with the introduction of oxygen at a partial pressure of 100 kg/cm$^2$G. The resultant product was transferred to a distillation apparatus, and unreacted o-xylene and the glacial acetic acid were removed by distillation at a bath temperature of 160°C. The bath temperature was then maintained at 200°C. and the pressure, at 1 mmHg. There was obtained 1.7 parts of tetramethyl diphenyl. The catalyst residue hardly contained any tetramethyl diphenyl. When the reaction was conducted under the same conditions using the recovered catalyst, there was obtained 1.6 parts of tetramethyl diphenyl, which corresponded to 815 mol % based on the palladium acetate fed.

EXAMPLES 32 to 37 AND COMPARATIVE EXAMPLE 4

These Examples illustrate the relation between the partial pressure of oxygen and the yields of the diphenyls for easy understanding.

A stainless steel autoclave equipped with a stirrer was charged with 10 parts of toluene, 32 parts of glacial acetic acid and 0.42 part of palladium acetate [Pd(AcO)$_2$], and the toluene was reacted for 10 hours at 110°C. with the introduction of oxygen at a partial pressure indicated in the following table. The results obtained are shown in the following table.

| Example No. | Oxygen partial pressure (kg/cm$^2$) | Dimethyldiphenyl produced (part) | Mol % of the product based on the catalyst |
|---|---|---|---|
| Comparative Example 4 | 0.8 | 0.366 | 107 |
| Example 32 | 2.0 | 0.619 | 181 |
| 33 | 2.5 | 0.616 | 180 |
| 34 | 4.5 | 0.650 | 190 |
| 35 | 6.5 | 0.729 | 213 |
| 36 | 15.0 | 0.672 | 196 |
| 37 | 30.0 | 0.661 | 193 |

EXAMPLES 38 TO 43 AND COMPARATIVE EXAMPLES 5 AND 6

These Examples also illustrate the relation between the partial pressure of oxygen and the yields of the diphenyls for easy understanding.

A stainless steel autoclave equipped with a stirrer was charged with 10 parts of toluene, 32 parts of glacial acetic acid and 0.654 part of palladium benzoate [Pd(C$_6$H$_5$COO)$_2$], and the toluene was reacted for the 6 hours at 130°C. with the introduction of oxygen at a partial pressure indicated in the following table. The results obtained are shown in the following table.

| Example No. | Oxygen partial pressure (kg/cm$^2$) | Dimethyldiphenyl produced (part) | Mol % of the product based on the catalyst |
|---|---|---|---|
| Comparative Example 5 | 0.8 | 0.346 | 101.2 |
| Example 6 | 1.9 | 0.380 | 111.2 |
| Example 38 | 4.5 | 0.945 | 276.3 |
| 39 | 7.0 | 0.831 | 243.0 |
| 40 | 14.5 | 0.528 | 154.4 |
| 41 | 20.0 | 0.522 | 152.7 |
| 42 | 30.0 | 0.519 | 151.8 |
| 43 | 50.0 | 0.608 | 177.8 |

EXAMPLE 44

A stainless steel autoclave equipped with a stirrer was charged with 10 parts of toluene, 32 parts of glacial acetic acid, 0.654 part of palladium benzoate [Pd(C$_6$H$_5$COO)$_2$] and 0.6 part of sodium acetate [CH$_3$COONa], and the toluene was reacted for the 6 hours at 130°C. with the introduction of oxygen at a partial pressure of 7.0 kg/cm$^2$G. Gas-chromatographic analysis of the product indicated the formation of 0.907 part of dimethyl diphenyl, which corresponded to 265.2 mol % of palladium acetate fed.

EXAMPLE 45

A stainless steel autoclave equipped with a stirrer was charged with 10 parts of toluene, 32 parts of glacial acetic acid, 0.654 part of palladium benzoate [Pd(C$_6$H$_5$COO)$_2$] and 0.60 part of sodium acetate [CH$_3$COONa], and the toluene was reacted for the 6 hours at 130°C. with the introduction of oxygen at a partial pressure of 20 kg/cm$^2$G. Gas-chromatographic analysis of the product indicated the formation of 0.713 part of dimethyl diphenyl, which corresponded to 208.4 mol % of palladium acetate fed.

We claim:
1. A process for producing diphenyls which comprises contacting benzene or a benzene derivative expressed by the following formula

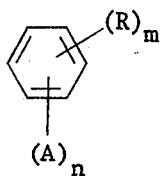

wherein R's may be the same or different and represent alkyl having 1 to 4 carbon atoms;
m is a positive integer of 0 to 4;
A's may be the same or different and represent alkoxy having 1 to 4 carbon atoms or a halogen atom;
n is a positive integer of 0 to 2; and the sum of m and n does not exceed 3, and when m is 0 or n is 0, $-(R)_m$ or $-(A)_n$ respectively represents a hydrogen atom,
with molecular oxygen, at a pressure of from 3 to 300 atmospheres calculated as the partial pressure of oxygen and at a temperature in the range of 100° to 300°C., in the presence of a catalyst comprising
1. at least one organic carboxylate of palladium (II) in an amount of $1 \times 10^{-5}$ to $1 \times 10^{-1}$ gram-atom, calculated as metallic palladium, per gram-mol of the benzene of the benzene derivative,
said organic carboxylate of palladium (II) being selected from palladium salts of mono- basic unsubstituted aliphatic carboxylic acids having not more than 20 carbon atoms which can be substituted by at least one of chlorine and fluorine, cyclohexane monocarboxylate, methyl cyclohexane monocarboxylate, benzoate, o-toluate, m-toluate, p-toluate, p-tertiary butylbenzoate, o-methoxybenzoate, m-methoxybenzoate, p-methoxybenzoate, chlorobenzoate and naphthoate, and
2. at least one zirconium (IV) compound in an amount of 0.01 – 100 gram-atoms, calculated as zirconium metal, per gram-atom of the palladium;
said zirconium (IV) compound being selected from the group consisting of
A. zirconium (IV) salts of oxyformic acid, oxyacetic acid, oxypropionic acid, oxy-n-butyric acid, oxy-isobutyric acid; and
B. oxychloride of zirconium (IV).

2. A process according to claim 1 wherein said oxidative coupling is carried out in the presence of an organic liquid medium which is a liquid at room temperature and is stable under the reaction conditions in an amount not in excess of 100 times the weight of said benzene or benzene derivative wherein said organic liquid medium is an organic carboxylic acid or an aqueous solution thereof containing less than 15% by weight of water.

3. A process according to claim 1 wherein said oxidative coupling is carried out at a temperature in the range of 110° to 250°C.

4. The process of claim 1 wherein said organic carboxylated palladium (II) is selected from the group consisting of palladium (II) salts of formate, acetate, trifluoroacetate, monochloracetate, propionate, n-butyrate, iso-butyrate, laurate, palmitate, and stearate.

* * * * *

UNITED STATES PATENT AND TRADEMARK OFFICE
CERTIFICATE OF CORRECTION

PATENT NO. : 3,963,787
DATED : June 15, 1976
INVENTOR(S) : ICHIKAWA, ET AL.

It is certified that error appears in the above—identified patent and that said Letters Patent are hereby corrected as shown below:

Claim 1, subparagraph 1, line 4, delete "of", insert -- or --

Signed and Sealed this

Seventh Day of September 1976

[SEAL]

Attest:

RUTH C. MASON
Attesting Officer

C. MARSHALL DANN
Commissioner of Patents and Trademarks